(12) United States Patent
Tadin

(10) Patent No.: US 6,904,692 B2
(45) Date of Patent: Jun. 14, 2005

(54) METHOD AND SYSTEM FOR CAPTURING AND SUPPORTING 3-D CONTOUR

(75) Inventor: Tony Tadin, Woodside, CA (US)

(73) Assignee: Amfit, Inc., Vancouver, WA (US)

( * ) Notice: Subject to any disclaimer, the term of this patent is extended or adjusted under 35 U.S.C. 154(b) by 0 days.

(21) Appl. No.: 10/871,556

(22) Filed: Jun. 18, 2004

(65) Prior Publication Data
US 2005/0022407 A1 Feb. 3, 2005

Related U.S. Application Data (60) Provisional application No. 60/479,386, filed on Jun. 18, 2003.

(51) Int. Cl.⁷ .............................. G01B 7/28; A61B 5/103
(52) U.S. Cl. ........................................ 33/515; 33/514.2
(58) Field of Search .................... 33/515, 552, 514.2

(56) References Cited

U.S. PATENT DOCUMENTS

| 2,330,317 A | * | 9/1943 | Stewart | 33/515 |
|---|---|---|---|---|
| 2,378,039 A | * | 6/1945 | Schneker | 33/514.2 |
| 4,454,618 A | | 6/1984 | Curchod | 12/1 R |
| 4,876,758 A | | 10/1989 | Rolloff et al. | 12/142 N |
| 5,640,779 A | | 6/1997 | Rolloff et al. | 33/514.2 |
| 6,160,264 A | * | 12/2000 | Rebiere | 33/515 |

* cited by examiner

Primary Examiner—Christopher W. Fulton
(74) Attorney, Agent, or Firm—Ohlandt, Greeley, Ruggiero & Perle, L.L.P.

(57) ABSTRACT

A three-dimensional (3-D) capture method and system having a 3-D contour capture device for capturing a surface contour of an object, a contoured support device for placing between the surface and the 3-D contour capture device that provides additional support to at least a portion of the surface, wherein a first contour captured by the 3-D contour capture device is modified based on a second contour captured with the contoured support device placed between the surface and the 3-D contour capture device to provide a resultant 3-D contour.

20 Claims, 12 Drawing Sheets

METHOD AND SYSTEM FOR CAPTURING AND SUPPORTING 3-D CONTOUR

CROSS-REFERENCE TO RELATED APPLICATIONS

This application claims priority to U.S. Provisional Patent Application Ser. No. 60/479,386 filed on Jun. 18, 2003.

BACKGROUND OF THE INVENTION

1. Field of the Invention

This invention relates to a 3-D (three-dimensional) contour capturing method and system and, more particularly, to a method and system that provides improved support in selective areas of the captured contour.

2. Description of Related Art

There are a number of methods and systems for capturing 3-D contours of subject objects. The subject object can be a variety of items, including inanimate objects and body parts. Regarding body parts, a 3-D contour of a foot may be desired in order to provide a customization of shoes and/or orthotics for the foot.

3-D contour measurement methods for the feet may include sampling the undersurface of the foot using mechanical (e.g., impression molds having plaster, sand, foam, etc.), electronic, electro-mechanical, electro-optical, and a combination thereof devices. One such method for capturing a 3-D contour of the underside or plantar surface of a foot is disclosed in U.S. Pat. Nos. 4,876,758 and 5,640,779, both of which are commonly assigned to the assignee of the present patent application and incorporated herein in their entirety. The U.S. Pat. Nos. 4,876,758 and 5,640,779 disclose a foot impression unit (e.g., a pin digitizer) having an array of gauge pin elements, a control mechanism for urging the gauge pins into contact with the undersurface of a person's foot to form an impression of the undersurface of the foot, a locking mechanism for releasably locking the gauge pins in place to retain that impression, and a sensing mechanism for scanning the gauging elements to produce digital signals indicative of the positions of the gauging elements.

The gauge pins of the pin digitizer measure a position of the foot placed thereon relative to a datum surface. The acquired measurements are processed to produce an accurate, preferably digital, model of the undersurface of the foot. The pin digitizer is able to accurately, by way of the gauge pins, deflect the soft tissue of the foot encountered by the gauge pins upwardly urged against the undersurface of the foot. This data set produced by the pin digitizer provides a 3-D contour that is supportive and corresponding to the soft tissue areas on the undersurface of the foot. The pin digitizer provides an accurate contour of a person's foot placed thereon. The accurately captured 3-D contour of the foot may then be used to form and/or customize orthotics, shoes, and the like.

It is noted that the gauge pins are typically urged upwardly uses a common methodology that urges all of gauge pins upwardly with a common force, rate, etc. Thus, it is not typically possible to provide selective differences to various gauge pins.

However, there exists a need to provide more than an accurate reproduction of the plantar surface of a foot. Such needs may arise due to problems associated with a person's foot. Some foot associated and/or body alignment problems may necessitate providing greater support in a certain area of the plantar surface of the foot than other areas thereof. For example, extra support may be required or desired in the arch region of the foot to correct or address ailments associated therewith.

Additional (i.e., extra) support may be desirable for improved support, stability and comfort in a foot orthotic. The difficulty in providing additional support is that heretofore it has been difficult to determine how much extra support the foot can tolerate and what areas of the foot can/should accept the extra support. Thus, determining how much and where to provided extra support to the foot typically requires the expertise of a foot specialist or one highly skilled in the production of foot support devices.

Accordingly, there exists a need to accurately provide additional support in a selective area of the plantar surface of the foot in acquiring a 3-D contour thereof.

SUMMARY OF THE INVENTION

The present disclosure provides a three-dimensional (3-D) capture system having a 3-D contour capture device for capturing a surface contour of an object, a contoured support device for placing between the surface and the 3-D contour capture device that provides additional support to at least a portion of the surface, wherein a first contour captured by the 3-D contour capture device is modified based on a second contour captured with the contoured support device placed between the surface and the 3-D contour capture device to provide a resultant 3-D contour.

The present teachings also provide a method for capturing a 3-D contour including placing an object on a 3-D contour capture device, acquiring a first contour of a surface of the object, placing a contoured support device between the surface and the 3-D contour capture device, supporting at least a portion of the surface on the contoured support device, the contoured support device providing additional support to at least a portion of the surface, acquiring a second contour of the surface of the object with the contoured support device placed between the surface and the 3-D contour capture device, and providing a resultant 3-D contour of the surface based on the second contour modifying the first contour.

These and other aspects of the present disclosure will be further understood when read in conjunction with the detailed description, claims, and accompanying drawings.

DETAILED DESCRIPTION OF THE INVENTION

Figure 1:
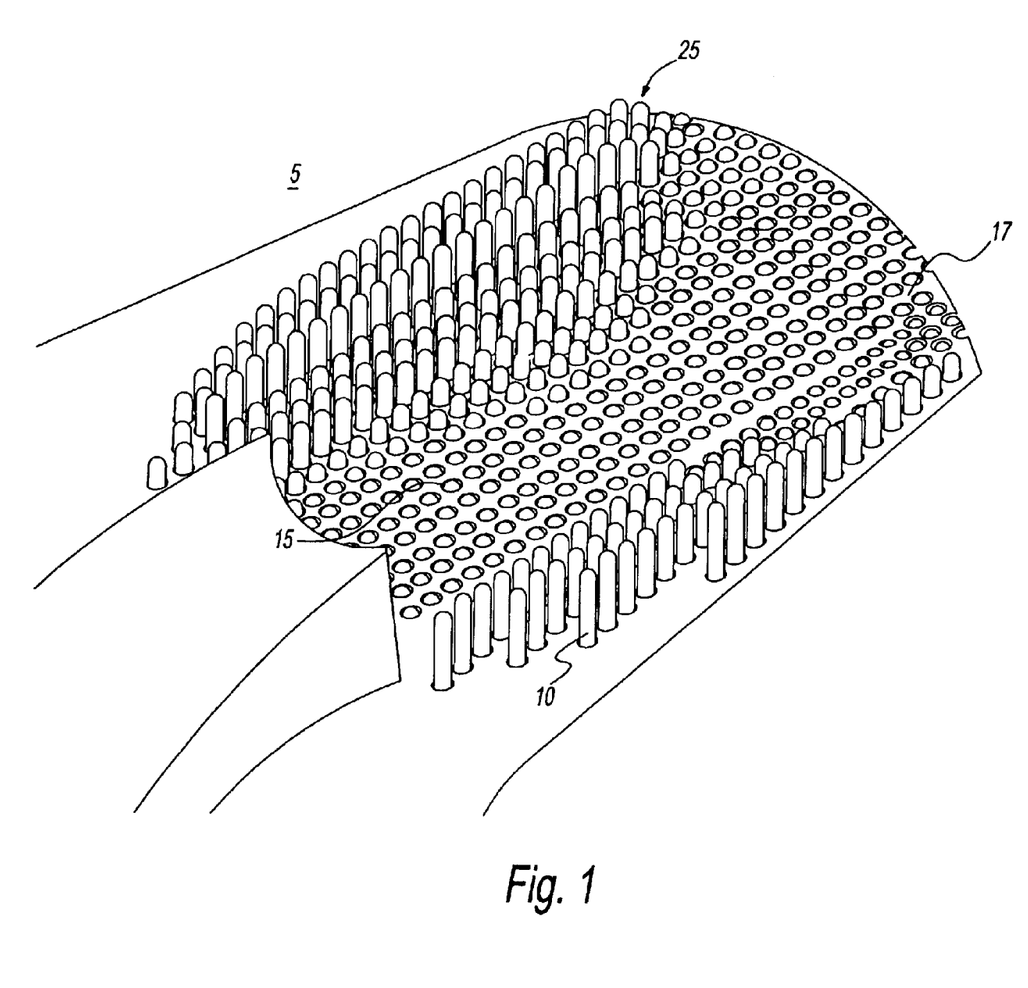
FIG. 1 is a top perspective view of an exemplary pin digitizer, including pin gauges for capturing the undersurface of an object, in accordance with the teachings herein.

A contoured support device is disclosed for providing support, preferably additional support, to the surface of an object having the contour thereof captured by a 3-D contour capture device. The contoured support device cooperates with the 3-D contour capture device to facilitate acquisition of 3-D contours of the subject object. FIG. 1 shows an exemplary 3-D contour capture device, represented generally by the reference numeral 5. 3-D contour capture device 5, first shown in FIG. 1, is a pin digitizer type of 3-D contour capture device. Pins 10 are urged upwardly through apertures 15 to contact a surface of the object having a surface thereof captured.

The object is placed on surface 17, pins 10 are urged upwardly through apertures 15 in surface 17. The upward motion of pins 10 is stopped when pins 10 contact the surface of the object placed on surface 17. The upward motion of pins 10 is stopped when pins 10 cannot overcome the normal force with which the surface of the object placed on surface 17 exerts downwardly on surface 17 and pins 10.

The subject object may be a variety of items, including inanimate structures and body parts. While the present disclosure will be discussed primarily in the context of acquiring 3-D contours of a person's foot, it should be clearly understood that the subject object is not limited to a foot.

FIG. 1 further illustrates an exemplary captured contour 25. Captured contour 25 is acquired by placing a foot (not shown) on surface 17, urging pins 10 upwardly through apertures 15 until pins 10 contact the undersurface of the foot, and locking or maintaining pins 10 in the stopped positions caused by contact with the foot. In this manner, captured contour 25 is obtained.

It is noted that gauge pins 10 are typically urged upwardly uses a common methodology that urges all of gauge pins 10 upwardly with a common force, rate, etc. Thus, it is not typically possible to provide selective differences to various gauge pins 10.

Figure 2:
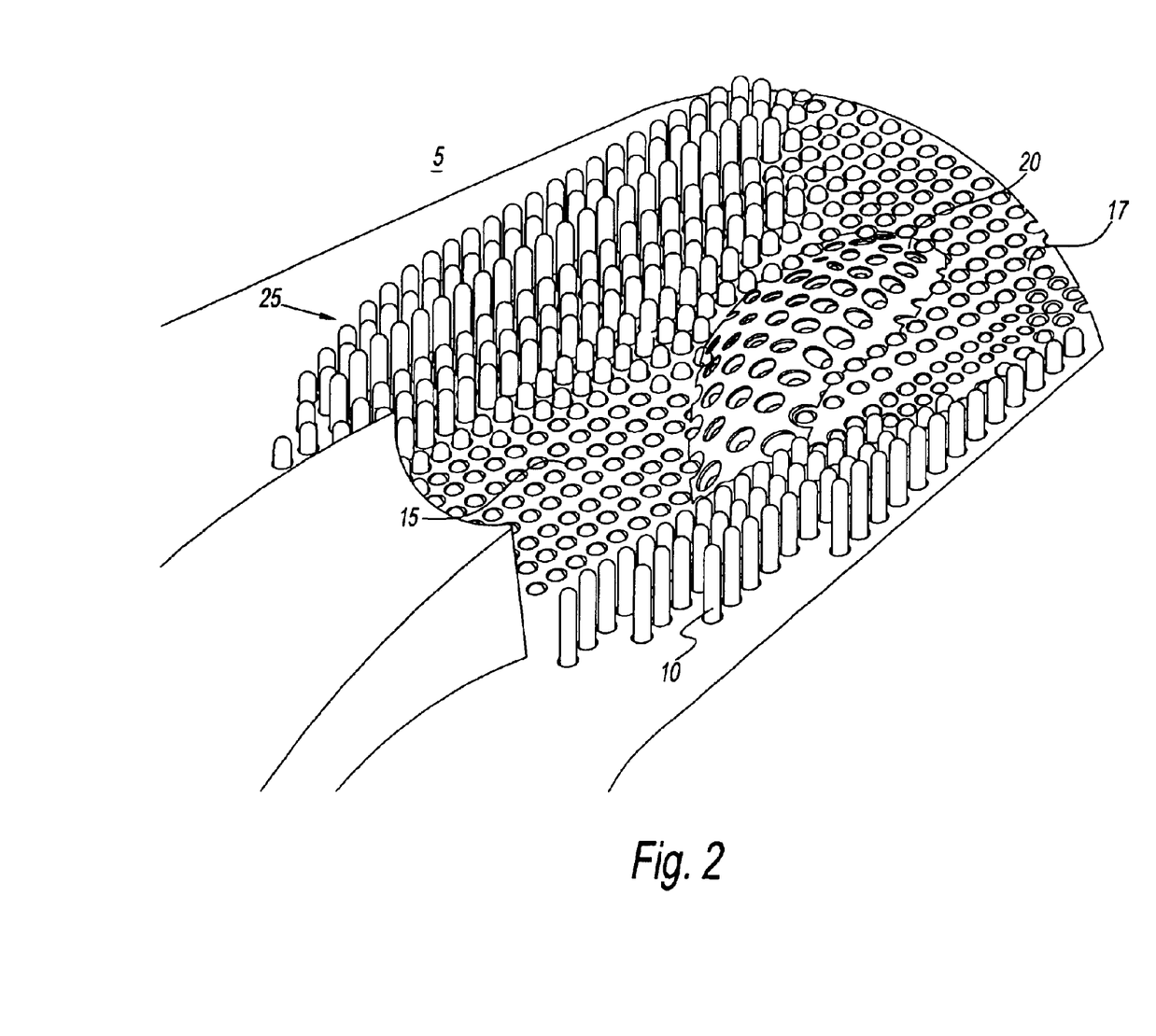
FIG. 2 is a top perspective view of the pin digitizer of FIG. 1 wherein contoured support device is placed thereon, in accordance with the teachings herein.

FIG. 2 shows an exemplary contoured support device 20. Contoured support device 20 provides support, preferably additional support, to the surface of the object (e.g., a foot) having the contour thereof captured by 3-D contour capture device 5. In one aspect hereof, contoured support device 20 is a shell of a resilient flexible material. The specific material used to construct contoured support device 20 can be varied. The resilient and flexible characteristic of contoured support device is preferred.

The particular shape of contoured support device 20 is designed to provide extra support to selected areas of the surface of the subject object. For example, contoured support device 20 may be particularly shaped and sized to provide support to the plantar surface of the foot. The contoured support device of FIG. 2, for example, extends over a portion of the space occupied by captured contour 25. That is, contoured support device does not, in this example, extend throughout the entirety of the surface 17 that the surface of the foot will contact. In this instance, contoured support device 20 only extends over a specific portion of the area that will be contacted by the foot.

Figure 3:
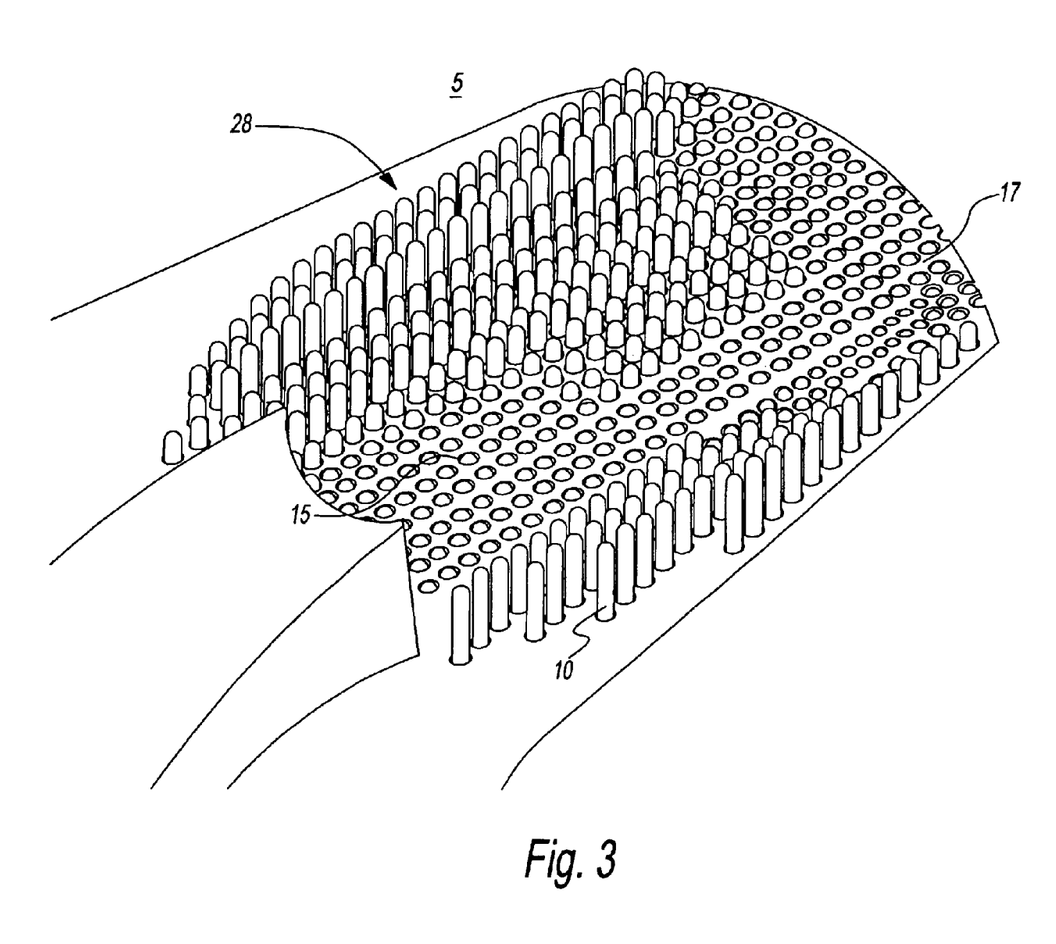
FIG. 3 is a top perspective view of the pin digitizer of FIG. 2 wherein the captured contour of the subject object placed on the contoured support device is illustrated, in accordance with the teachings herein.

FIG. 3 illustrates a captured contour 28, acquired by capturing a 3-D contour of the underside of the foot placed on and supported by contoured support device 20. Captured contour 28 is obtained using the contoured support device of FIG. 2.

Contoured support device 20 can be shaped and sized in a variety of configurations, depending on the context of use, desired result, desired areas that will be supported, and/or application.

Figure 4:
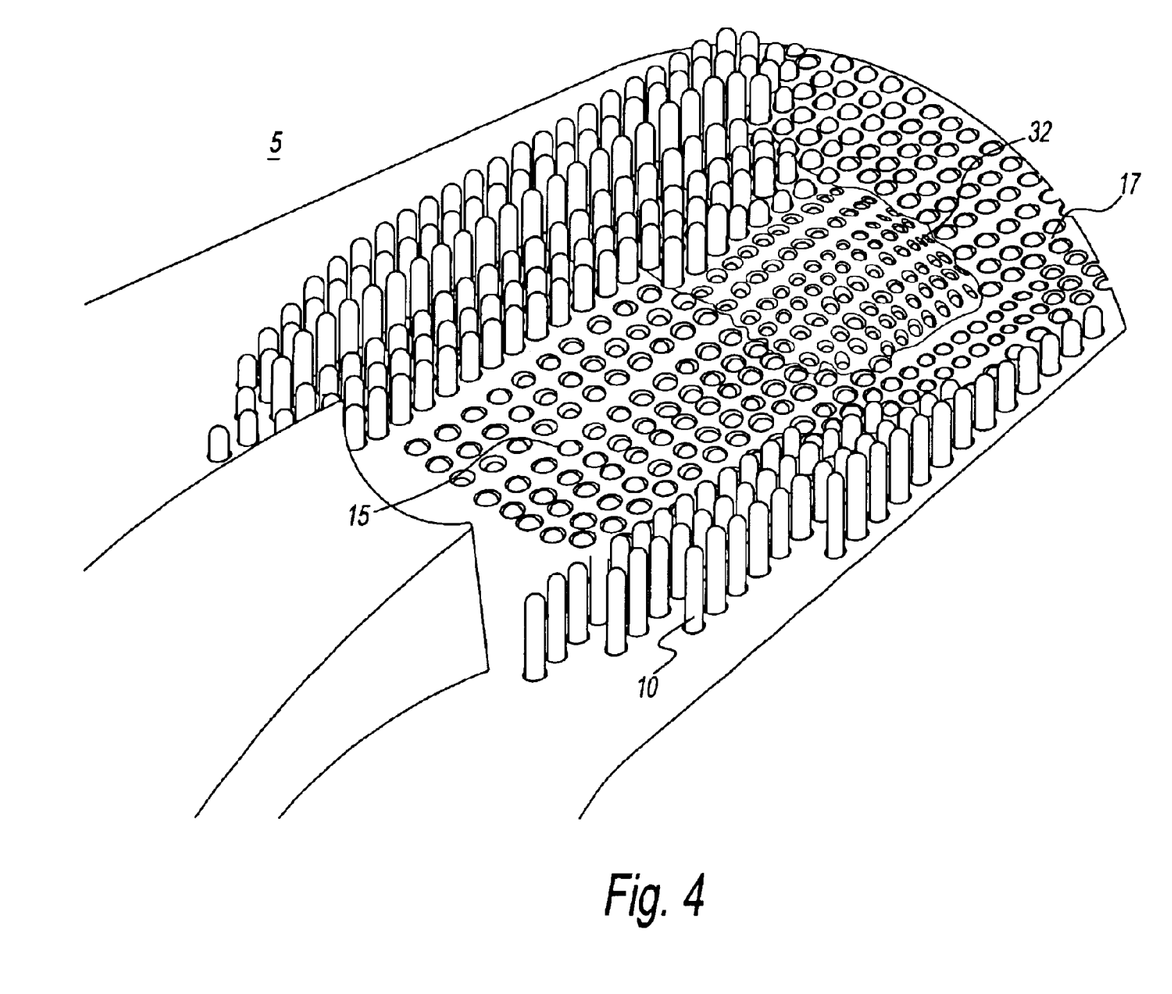
FIG. 4 is a top perspective view of the pin digitizer of FIG. 1 wherein a contoured support device of a second configuration is placed thereon, in accordance with the teachings herein.
Figure 5:
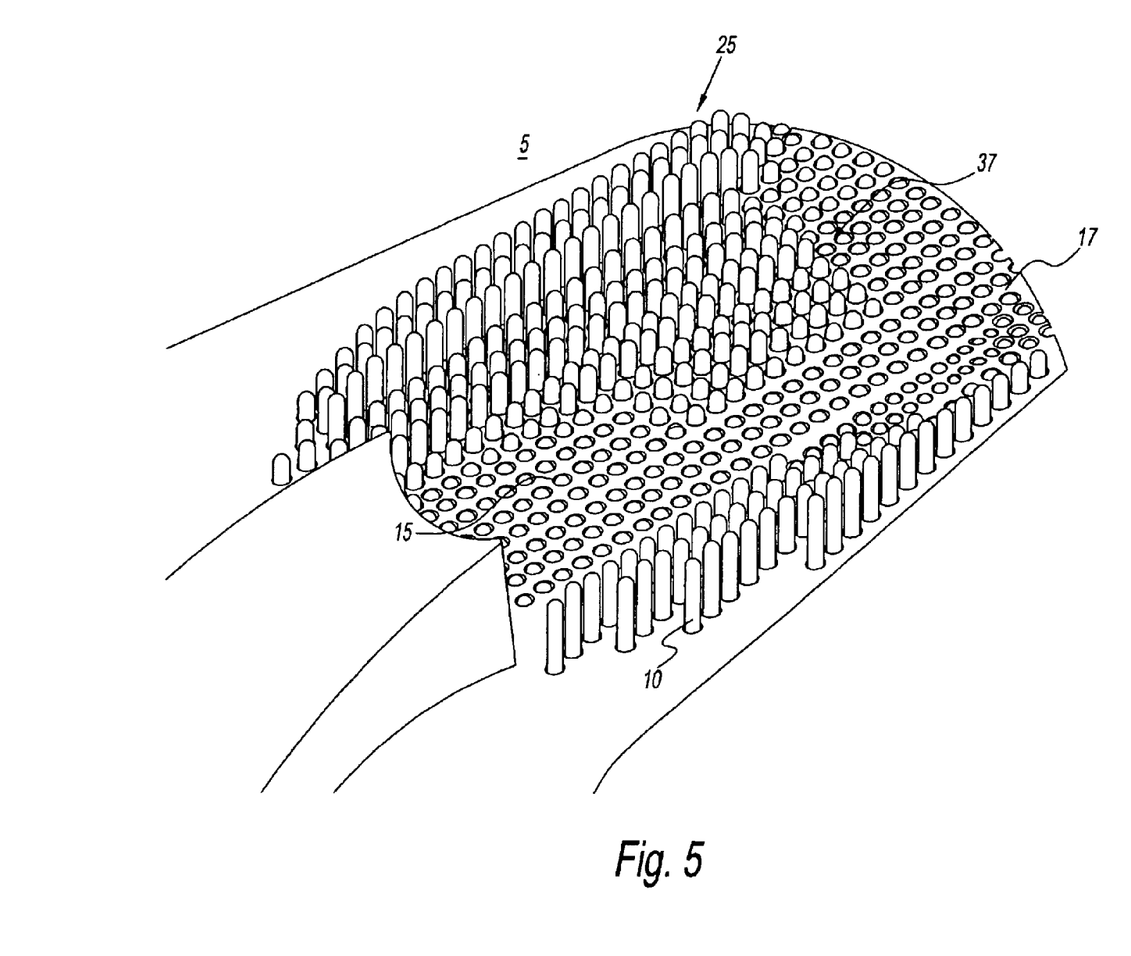
FIG. 5 is a top perspective view of the pin digitizer of FIG. 4 wherein the captured contour of the subject object placed on the second contoured support device thereof is illustrated, in accordance with the teachings herein.

FIG. 4 illustrates a contoured support device 32 having a shape and size different than that of contoured support device shown in FIG. 2. FIG. 5 illustrates an exemplary 3-D contour 37 captured using contoured support device 32 of FIG. 4.

In one aspect hereof, contoured support devices 20, 32 act like a spring when placed under the subject foot (or other object). That is, due to the preferably resilient characteristic of contoured support device 20, 32, contoured support device 20, 32 are flexible, at least in portions thereof. Contoured support device 20, 32 can flex in response to a force applied thereto. Contoured support device 20 will preferably flex (e.g., deflect) in response to a force greater than a minimum threshold force. When the applied force exceeds the minimum threshold, then contoured support device 20, 32 are deflected in the in response thereto, substantially in direction indicated by arrow 30 in FIGS. 6 and 7.

The minimum threshold force is preferably in the rage of 1.5 to 3.0 pounds per square inch (psi), with a most preferred range of 2.0 to 2.5 psi.

Figure 6:
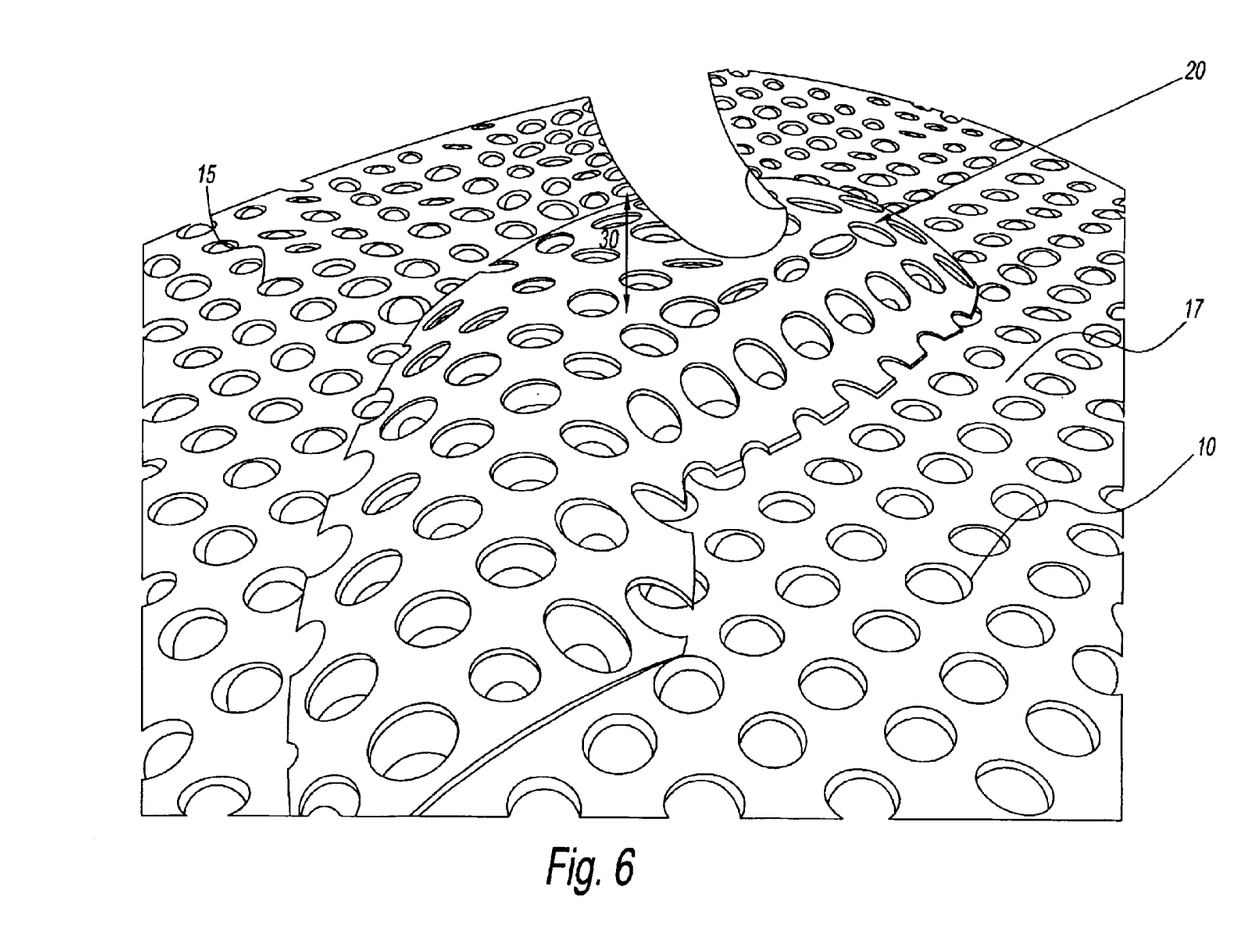
FIG. 6 is a top perspective, detailed view of an exemplary contoured support device, in accordance with the teachings herein.

FIG. 6 shows a top perspective view of exemplary contoured support device 20, in an un-flexed position. That is, the convex, dome-like shape of the upper contact surface of contoured support device 20 is shown in detail.

In an aspect hereof, contoured support device 20 acts like a spring having a spring rate (i.e., spring constant) selected such that contoured support device 20 can deflect soft tissue (e.g., fleshy skin and muscle) and yet support the underlying bone structure. The contoured support device 20 deflects the soft tissue, supports the bone structure, and collapses (i.e., flexes away from the foot in response to force applied by the foot) when a desired (optimal) support level is achieved.

Figure 7:
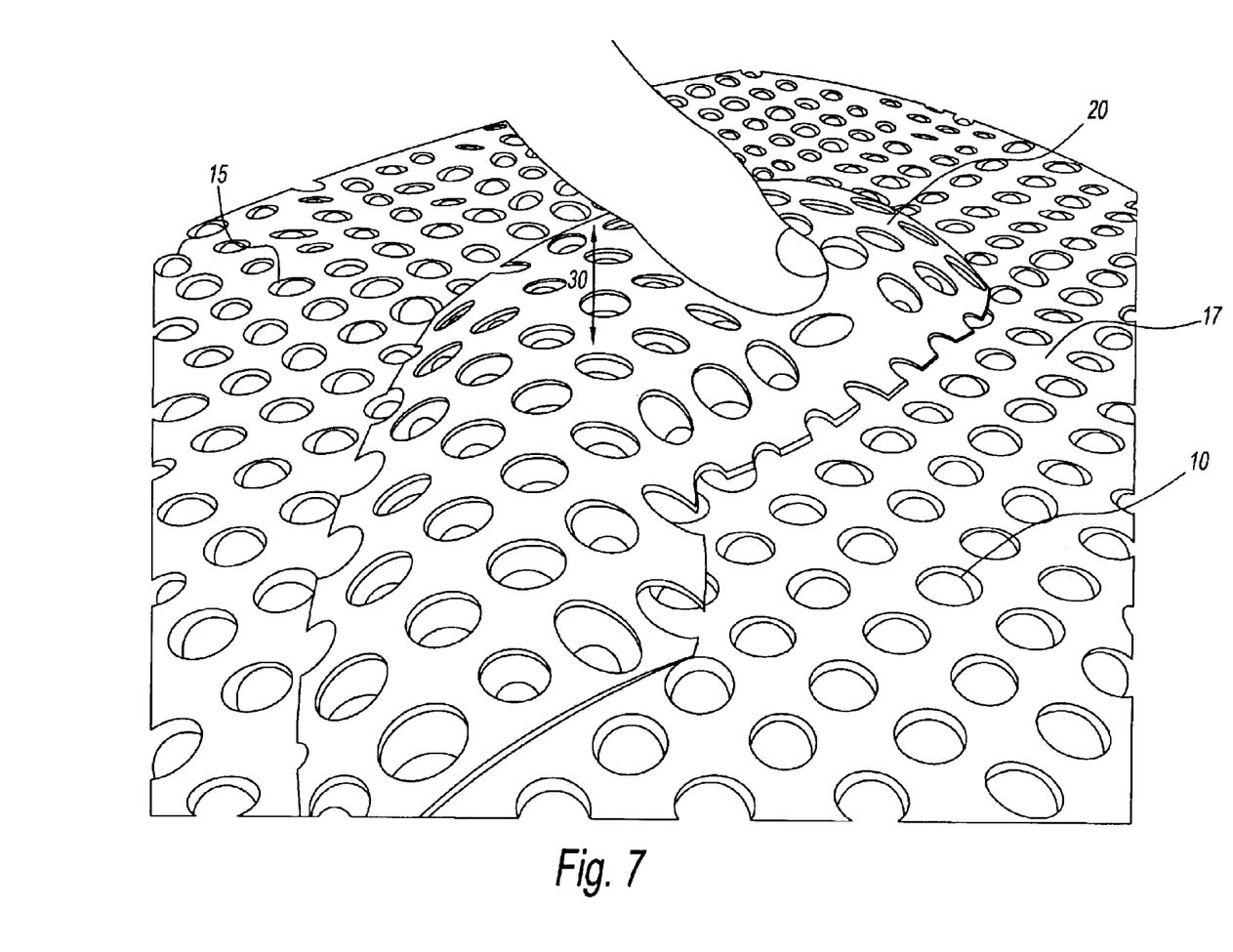
FIG. 7 is a top perspective view of the exemplary contoured support device of FIG. 6 in a flexed state, in accordance with the teachings herein.

FIG. 7 shows a top perspective view of exemplary contoured support device 20, in a flexed state or position. The convex, dome-like shape of the upper contact surface of contoured support device 20 is shown flexed or deflected downward in FIG. 7

The preferred spring rate can be accomplished by selective construction and configuration of contoured support device 20, 32. Such construction methods and processes may include thinning and other strength weakening/strengthening techniques to contoured support device 20, 32.

In another aspect hereof, the upward urging of gauge pins 10 may be adjustable, dynamically or predetermined, to adjust the amount of support provided by gauge pins 10.

As shown in FIGS. 2, 4, and 6, contoured support device 20, 32 are perforated to cooperate with 3-D contour device 5 such that the acquisition of contours thereby is not encumbered but, preferably, facilitated. The perforation pattern of contoured support device 20, 32 is configured to allow the free movement of gauge pins 10 through the contoured support device.

Operatively placed with pin digitizer 5, contoured support device 20, 32 provides a structure and method to accurately capture the plantar surface of the foot and provide additional, beneficial support to select areas of the foot.

The selected contoured support device, for example contoured support devices 20 and 32, can be placed on pin digitizer 5, using the contour captured (e.g., captured contour 25) prior to placement of contoured support device 20, 32 as a guide. That is, the contour 25 first captured without the use of contoured support device 20, 32 can be used a reference for the proper positioning of contoured support device 20, 32. The first captured contour 25 provides an accurate 3-D contour rendering of the underside of the foot. Contoured support device 20, 32, selected for the shape, size, and resiliency thereof, can be placed in the proper position, using the first captured contour 25 as a guide.

With contoured support device 20, 32 properly positioned on surface 17, the foot is placed on 3-D contour capture device 5. The foot's plantar surface is at a higher elevation in the area where contoured support device 20, 32 is present, due to the additional upward force provided thereby. The locking means of 3-D contour capture device 5 are released and gauge pins 10 are urged upwards again. The gauge pins elevate further to capture the newly supported undersurface of the foot in the area of contoured support device 20, 32. As shown in FIGS. 3 and 5, the contours obtained using contoured support devices 20 and 32 is higher in the areas supported by contoured support devices 20 and 32.

The 3-D contours of the foot acquired in accordance herewith are can be taken with the full load or weight or partial (i.e., semi-weighted) of the person applied to the foot. The full weight or force tends to flatten the underside of the foot. The contoured support device 20, 32 of the present disclosure provides support and restores support to an area (s) of the foot supported by the contoured support device. The contoured support device can be positioned and sized to provide support to the arch area of the foot.

Gauge pins 10 are again locked and the elevations of each gauge pin 10 is determined. The position of gauge pins 10 can be determined using mechanical, electro-mechanical, optical, or a number of techniques and processes.

It should be noted that for uniformity of discussion and comparison, all of the figures of this disclosure use the same subject foot so that a direct comparison of effect(s) of using contoured support device 20, 32 is clearly illustrated.

Figure 8:
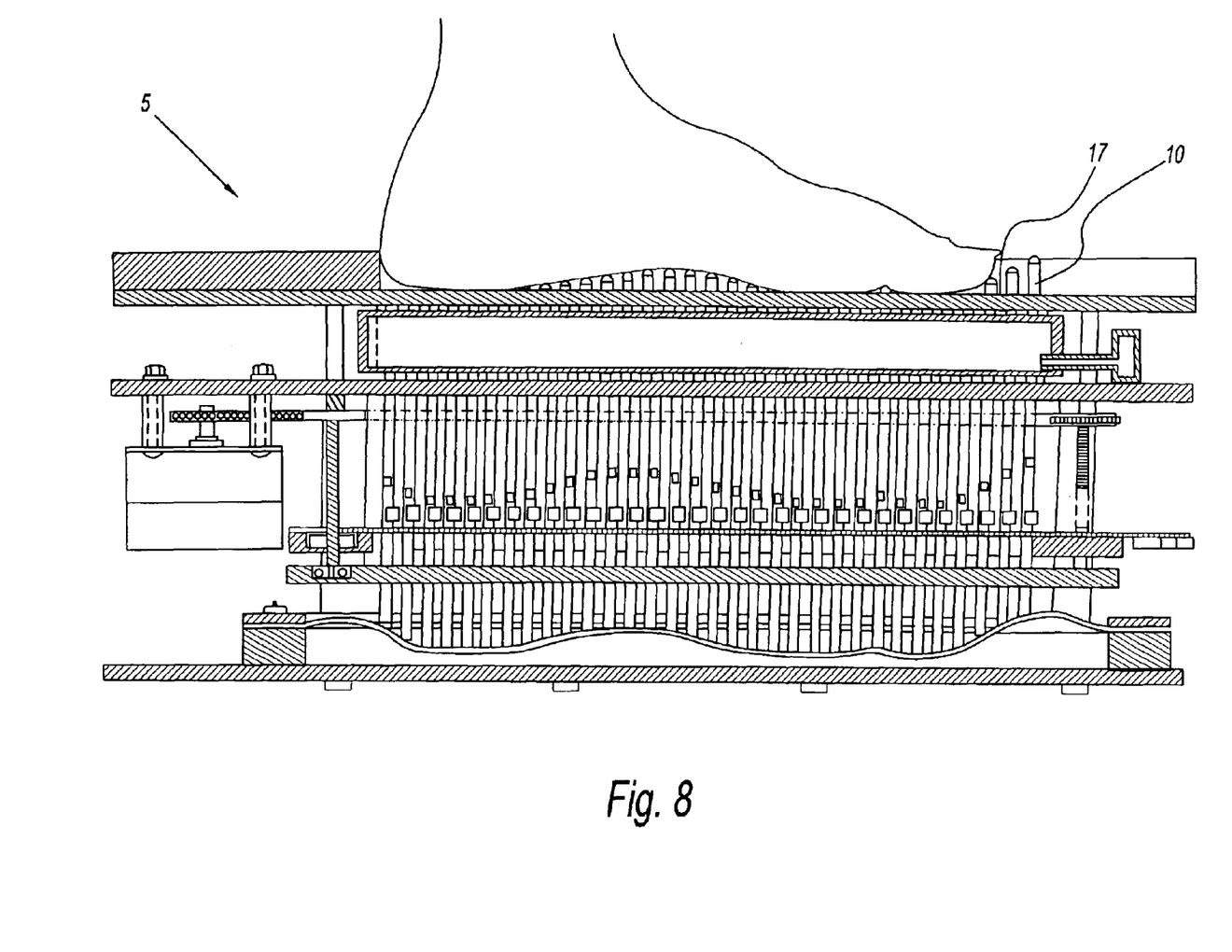
FIG. 8 is a cross-sectional side view of an exemplary pin digitizer with a foot placed thereon, in accordance with the teachings herein.

FIG. 8 illustrates a schematic side view of the foot placed upon the exemplary pin digitizer 5. The illustrated profile shows an exemplary depiction of the support provided by gauge pins 10 of pin digitizer 5, without the addition of a contoured support device.

Figure 9:
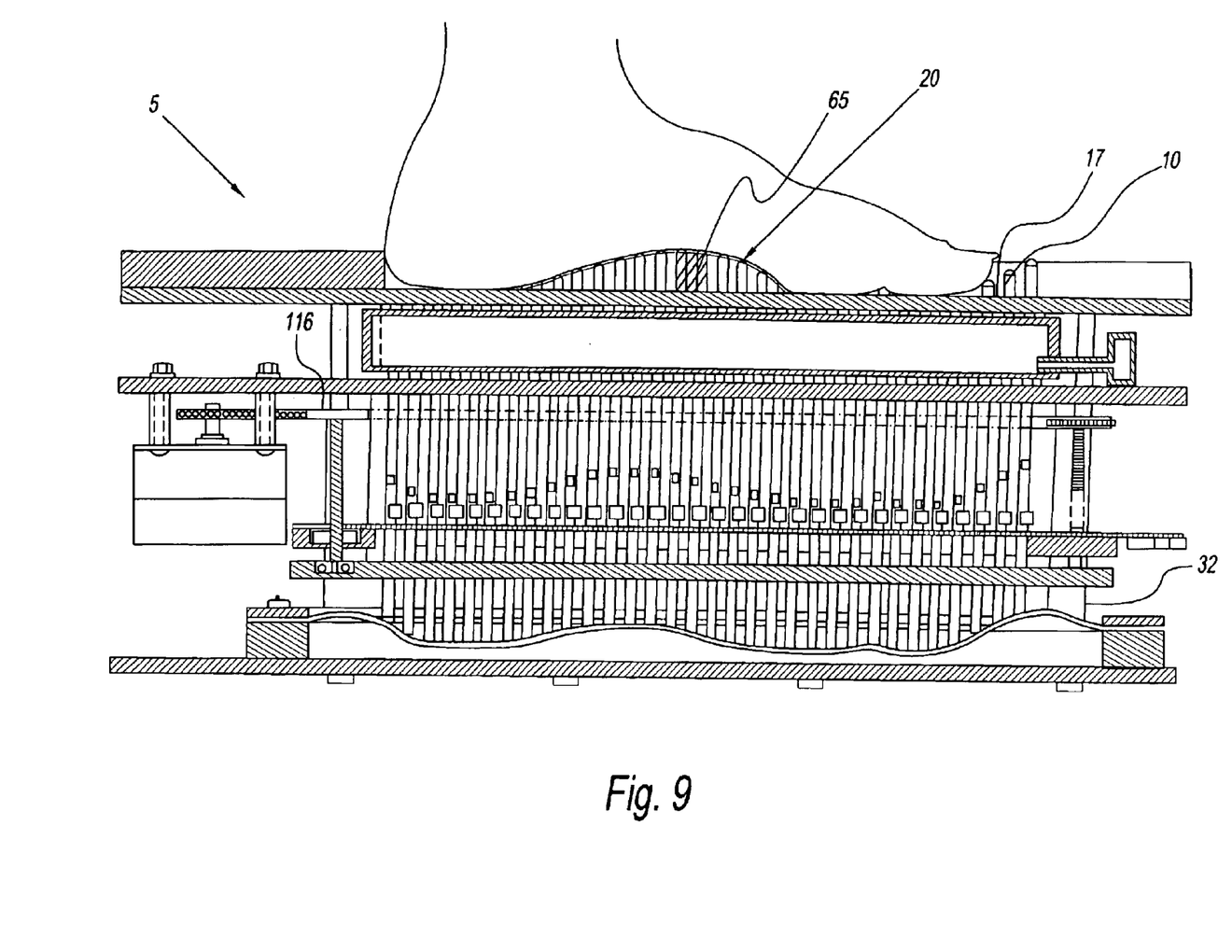
FIG. 9 is a cross-sectional side view of the exemplary pin digitizer of FIG. 8 with a foot placed on an exemplary contoured support device, in accordance with the teachings herein.

FIG. 9 illustrates a schematic side view of the foot placed upon the exemplary pin digitizer 5 showing the support provided by gauge pins 10 and contoured support device 20.

The method for capturing the 3-D contour can be summarized as including placing an object on a 3-D contour capture device and acquiring a first contour of a surface of the object. The method further includes placing the contoured support device (e.g., contoured support device 20 and 32) between the undersurface of the foot and 3-D contour capture device 5 and supporting at least a portion of the surface on the contoured support device thereon. The contoured support device selectively provides additional support to at least a portion of the undersurface of the foot. A second contour of the undersurface of the foot, with the contoured support device 20, 32 placed between the foot undersurface and 3-D contour capture device 5 is obtained. A resultant 3-D contour of the undersurface of the foot, based on the second contour modifying the first contour, is then determined.

The resulting 3-D captured contour and/or data representative thereof can be used to direct an automated machining system to produce a customized foot orthotic, shoe, etc. using the improved support characteristics obtained by the 3-D contour capture device and contoured support device 20, 32.

Figure 10:
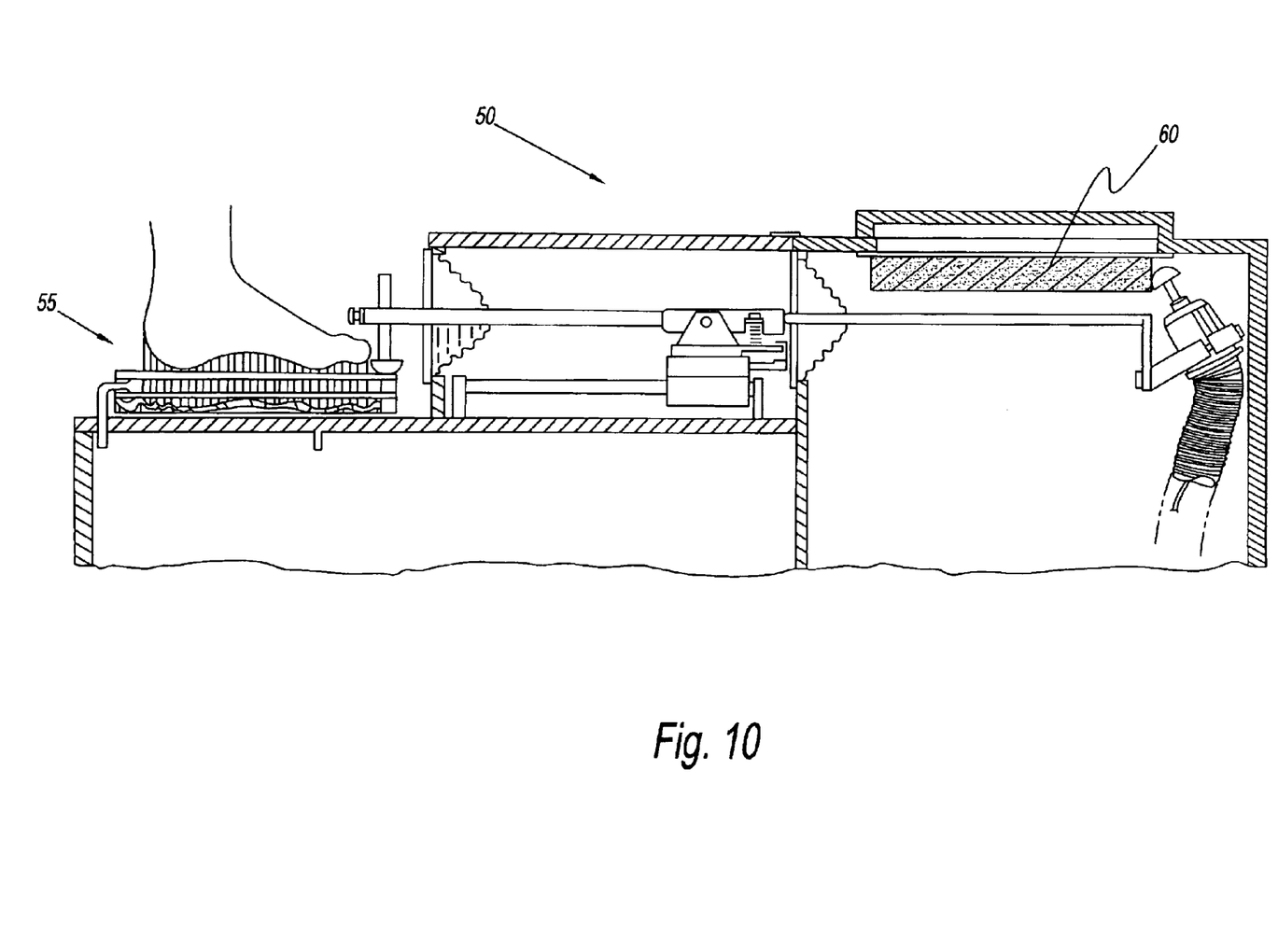
FIG. 10 is a cross-sectional side view of an exemplary 3-D contour duplicating device, in accordance with the teachings herein.
Figure 11:
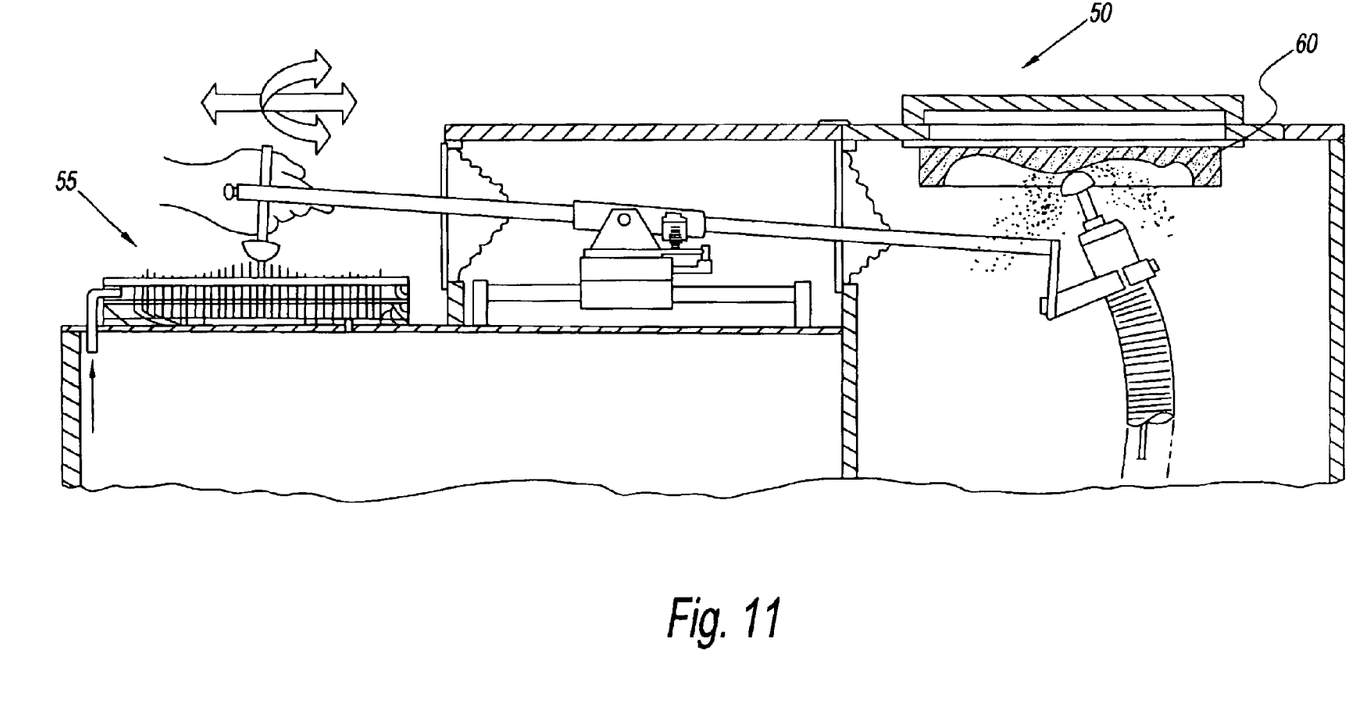
FIG. 11 is cross-sectional side view of the exemplary 3-D contour duplicating device of FIG. 10 being manipulated to duplicate the captured contour in a blank of material, in accordance with the teachings herein.

In an aspect hereof, a variety of manufacturing techniques, such as those disclosed in U.S. Pat. No. 4,454,618, assigned to the assignee of the present patent application disclosure, are applicable to and can be adapted to the teachings of the disclosure herein. The 3-D contour manufacturing process of U.S. Pat. No. 4,454,618 uses a 3-D trace routing machine 50, shown in FIGS. 10 and 11, to acquire a 3-D contour of the underside of the foot. Trace routing machine 50 uses a pin assembly having a locking mechanism. Instead of digitizing the relative positions of gauge pins 55 thereof as is the case with pin digitizer 5, trace routing machine 50 uses gauge pins 55 as a pattern or template. The pattern or template is duplicated in a block of material 60 (i.e., a blank) to fabricate, for example, a foot orthotic.

In an aspect hereof, the contoured support device is a flexible material that can be further supported above the gauge pins by an auxiliary support device 65, as shown in FIG. 9. Auxiliary support device 65 can be used selectively, in instances where an additional support is desired in certain areas of the contoured support device 20, over and beyond that provided by the contoured support device alone. Auxiliary support device 65 may have a number of embodiments. For example, a coil spring (not shown), an appropriately sized or perforated foam block, leaf spring, and other devices having spring-like characteristics can be placed beneath contoured support device 20, 32 to selectively enhance the support provided thereby.

A benefit of the combined use of auxiliary support device 65 and contoured support device 20 is to avoid capturing a contour having flat spot or area in the resulting contour capture. In this manner the contoured support device may be further customized to the particular application and context, in an effort to provide a highly customized and personal orthotic. to avoid capturing a contour having flat spot or area in the resulting contour of the foot. Auxiliary support device 65 can be constructed of blocks of plastic material and selectively placed at desired location of the contoured support device 20, particularly in the area of the heel.

Figure 12:
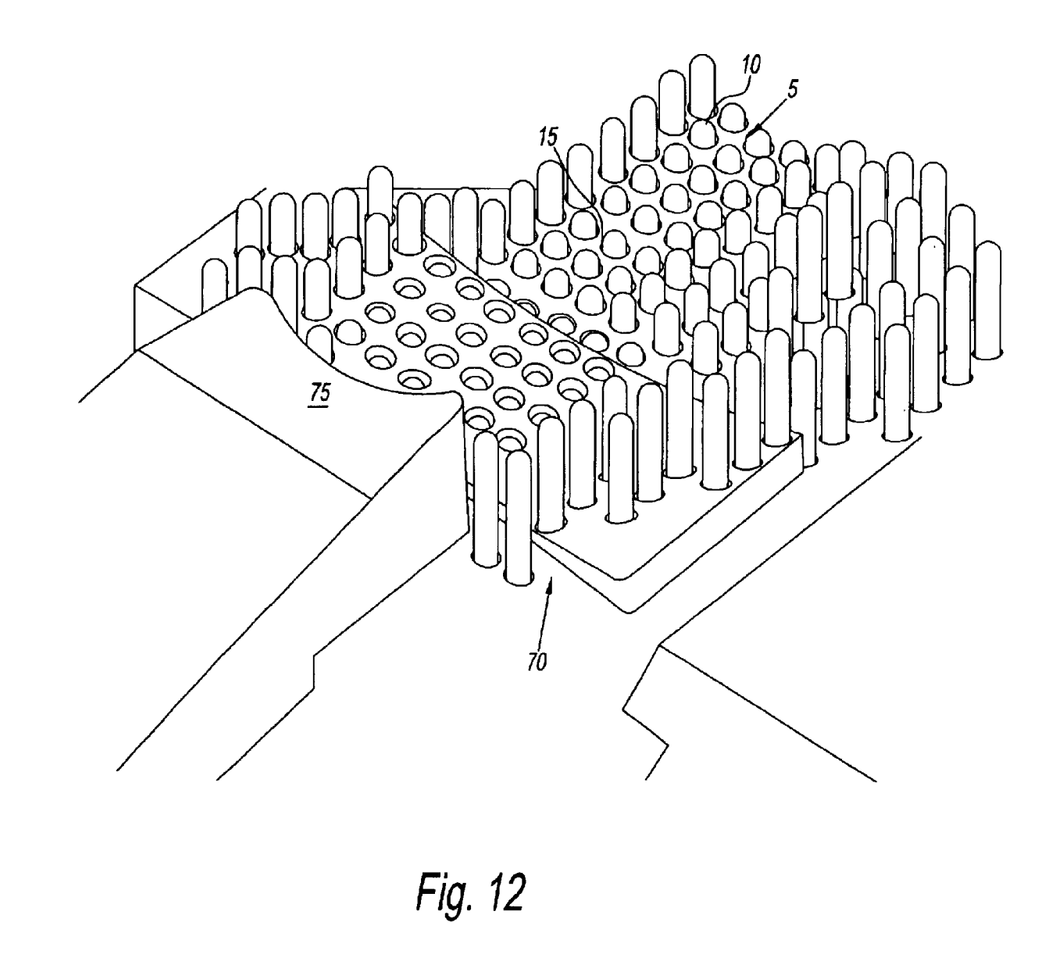
FIG. 12 is a top perspective view of an exemplary contoured heel support device.

In an aspect of the present disclosure, the contoured support device is configured to provide support to the heel area of the foot. Referring to FIG. 12, the contoured support device for supporting the heel, identified as contoured heel support device 70, is positioned on contour capture device 5 at a location that coincides with the heel strike area thereof. As illustrated, contoured heel support device 70 is located in close proximity to heel positioning device 75.

Contoured heel support device 70 preferably has a resilient middle section. The resilient middle section can be concave. The peripheral sides of contoured heel support 70 preferably provide greater support to the heel along the lateral and medial sides of the heel than the middle area of the heel. One method of providing greater support to the heel along the lateral and medial sides thereof is by providing contoured heel support 70 having sides thicker than the middle section of the contoured heel support device 70, as shown in FIG. 12. Other methods of providing support to the heel along the lateral and medial sides thereof include providing support blocks and/or other support structures (not shown) at the peripheral sides of contoured heel support device 70 that prevent, or at least limit, contoured heel support device 70 from completely flattening out at the lateral and medial sides of the foot during a contour capture of the foot. Preferably, contoured heel support device 70 is at a lowest point underneath the middle section of contoured heel support device 70 and rises to higher elevations as contoured heel support device 70 radiuses the heel to the medial and lateral sides thereof. Contoured heel support device is selectively elevated or otherwise supported to a greater extent along the medial and lateral sides thereof, for providing greater support to the foot along the medial and lateral sides of the foot.

In an aspect of the present disclosure, the 3-D contours captured by contour capture device 5 are digitized. The digital representations of the captured contours can be saved to a memory location, displayed for viewing on a display screen, provided to a printer for printing thereof, and further processed.

In one aspect hereof, in accordance with the methods of the present disclosure, the digital representation of the 3-D contour captured first without the contoured support device is saved to memory, the contoured support device (e.g., 20, 32, 70) is placed between the surface of the object being captured (e.g., a foot) and the contour capture device 5, and the 3-D contour of the object surface with the contoured support device positioned between the object and the contour capture device 5 is captured, digitized and saved to memory. The first captured and second captured 3-D contours can be displayed on a common display in, for example, split-screen, separate "windows", super-imposed one on the other, etc., for comparing the first and second captured 3-D contours.

It is also considered herein that an impression of a subject object, for example a foot, may include a full impression of the subject object or an partial portion thereof such as a partial length impression of a foot impression.

The claims appended hereto complement and further disclose the teachings of the present invention. The entirety of the application is to be considered regarding the scope, intent and disclosure of the present application.

What we claim is:

1. A three-dimensional (3-D) capture system comprising:
   a 3-D contour capture device for capturing a surface contour of an object;
   a contoured support device for placing between said surface and said 3-D contour capture device that provides additional support to at least a portion of said surface, wherein a first contour captured by said 3-D contour capture device is modified based on a second contour captured with said contoured support device placed between said surface and said 3-D contour capture device to provide a resultant 3-D contour.

2. The system of claim 1, wherein said 3-D capture device is selected from the group consisting of: a pin digitizer, an optical digitizer, and a mechanical trace duplicator.

3. The system of claim 1, wherein said contoured support device comprises a convex surface for contacting said surface of said object.

4. The system of claim 1, wherein said contoured support device has a resilient surface for supporting said surface of said object.

5. The system of claim 1, wherein said contoured support device matingly interfaces with said 3-D capture device.

6. The system of claim 1, wherein said contoured support device facilitates the acquisition of said second contour capture.

7. The system of claim 1, wherein said contoured support device supports said surface placed thereon, and applied with a predetermined, known range of force, in a first support position.

8. The system of claim 7, wherein said contoured support device supports said surface placed thereon, and applied with a force greater than said predetermined, known range of force, in a second support position.

9. The system of claim 1, wherein said contoured support device can be varied in size to accommodate a plurality of objects having a plurality of surface sizes.

10. The system of claim 1, further comprising an auxiliary support device for providing support, in addition to the additional support provided by said contoured support device.

11. A method for capturing a 3-D (three-dimensional) contour comprising:
    placing an object on a 3-D contour capture device;
    acquiring a first contour of a surface of said object;
    placing a contoured support device between said surface and said 3-D contour capture device;
    supporting at least a portion of said surface on said contoured support device, said contoured support device providing additional support to said at least a portion of said surface;
    acquiring a second contour of said surface of said object with said contoured support device placed between said surface and said 3-D contour capture device; and
    providing a resultant 3-D contour of said surface based on said second contour modifying said first contour.

12. The method of claim 11, wherein said 3-D capture device is selected from the group consisting of: a pin digitizer, an optical digitizer, and a mechanical trace duplicator.

13. The method of claim 11, further comprising saving said first contour for modification using a mechanical device, a memory device, or a combination thereof.

14. The method of claim 11, further comprising selecting said contoured support device having a desired combination of shape, size, and resiliency.

15. The method of claim 11, wherein said contoured support device comprises a convex surface for contacting said surface of said object.

16. The method of claim 11, wherein said contoured support device has a resilient surface for supporting said surface of said object.

17. The method of claim 11, wherein said contoured support device supports said surface placed thereon, and applied with a predetermined, known range of force, in a first support position.

18. The method of claim 17, wherein said contoured support device supports said surface placed thereon, and applied with a force greater than said predetermined, known range of force, in a second support position.

19. The method of claim 17, wherein said first contour, said second contour, and said resultant contour are saved to a memory device, said memory device selected from the group consisting of: mechanical, electro-mechanical, and electronic memory devices.

20. The method of claim 11, further comprising placing an auxiliary support device between said contoured support device and said 3-D contour capture device, said auxiliary support device providing support, in addition to said additional support provided by said contoured support device.

* * * * *